United States Patent [19]

Daines

[11] Patent Number: 5,700,943

[45] Date of Patent: Dec. 23, 1997

[54] PROCESS FOR MAKING PHENYLTHIOMETHYLPYRIDINYL-ALKENOATES

[75] Inventor: Robert A. Daines, Lansdale, Pa.

[73] Assignee: SmithKline Beecham Corporation, Philadelphia, Pa.

[21] Appl. No.: 356,353

[22] PCT Filed: Jun. 30, 1993

[86] PCT No.: PCT/US93/06177

§ 371 Date: Dec. 20, 1994

§ 102(e) Date: Dec. 20, 1994

[87] PCT Pub. No.: WO94/00433

PCT Pub. Date: Jan. 6, 1994

[51] Int. Cl.$^6$ ............ C07D 213/30; C07D 213/32; C07D 213/55; C07D 213/65

[52] U.S. Cl. ............ 546/296; 546/301; 546/302; 546/339; 546/340; 546/276.4

[58] Field of Search ............ 546/301, 296, 546/339, 340, 276.4

[56] References Cited

PUBLICATIONS

Journal of Organic Chemistry, vol. 3, Issued 1988, Trost et al., "Tetra–n–butylammonium Oxone. Oxidations under Anhydrous Conditions", pp. 532–537, esp. p. 535.

*Primary Examiner*—Alan L. Rotman
*Attorney, Agent, or Firm*—James M. Kanagy; Stephen Venetianer; Edward Lentz

[57] ABSTRACT

This invention relates to a process of making a compound of formula I (I)

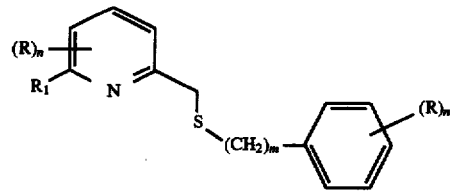

where $R_1$ contains an $\alpha,\beta$-unsaturated carbonyl group & $R_n$ is hydrogen or nonhydrogen radicals which do not have a functional group which interferes with the coupling reaction, which process comprises coupling a thiolphenol or phenylalkylmercaptan with a chloromethylpyridine in the presence of DBU under an inert atmosphere. These compounds are leukotriene antagonists and as such can be used in treating various diseases associated with leukotrienes.

7 Claims, No Drawings

PROCESS FOR MAKING PHENYLTHIOMETHYLPYRIDINYL-ALKENOATES

SCOPE OF THE INVENTION

The field of this invention is that of a process for making certain thioethers by coupling a chloromethyl pyridyl compound with thiophenols and related mercaptans. The products of this coupling, the thioethers and their related sulfoxides and sulfones are useful for treating diseases arising from or related to leukotrienes, particularly leukotriene $B_4$. As such there utility lies in antagonizing the affects of leukotrienes.

BACKGROUND OF THE INVENTION

A series of thioethers represented by the general formula

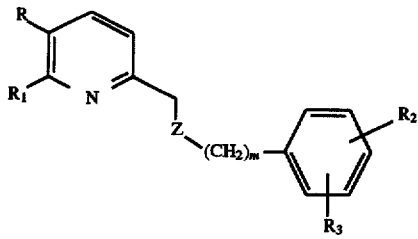

have been discovered to be useful in treating diseases involving the leukotriene cascade, particularly those diseases believed to be associated with or caused by the dihydroxyleukotrienes (leukotriene $B_4$). These thioethers can be found in certain publications, particularly PCT application Ser. No. PCT/US91/03772. A method for preparing those novel therapeutic agents is disclosed therein along with a description of utility and the background of the family of bioactive lipids known as the leukotrienes.

This invention relates to a process for making these compounds and other compounds of a similar nature where a chloromethylpridine is coupled with a thiophenol or benzylic mercaptan.

SUMMARY OF THE INVENTION

This invention covers a method for making a compound of formula I

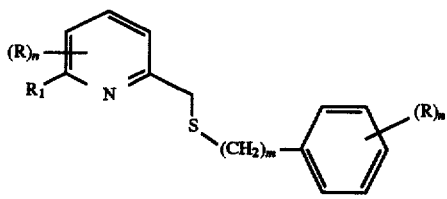

where $R_1$ contains an $\alpha,\beta$-unsaturated carbonyl group and the designation $(R)_n$ indicates hydrogen or one or more non-hydrogen radicals capable of being covalently bonded on the pyridyl and phenyl rings and m is 0–5; which method comprises coupling a chloromethylpyridine of formula II with a thiol of formula III in the presence of 1,8-diazabicyclo[5.4.0]undec-7-ene (DBU) under an inert gas at a temperature between about ambient and 100° C. for a period sufficient to effect the coupling.

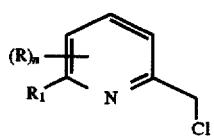

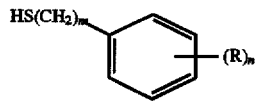

where $R_1$ is defined above and $(R)_n$ is hydrogen or one or more radicals which can be substituted on either the pyridyl or phenyl ring and m is 0–5.

GENERAL EMBODIMENTS

The following definitions are used in describing this invention.

An $\alpha,\beta$-unsaturated carbonyl group is illustrated by —CH=CH—C(=O)— or —C≡C—C(=O)—. The undefined carbonyl function valence can be a carbon—carbon bond, a carbon-heteroatom bond wherein the heteroatom is oxygen, nitrogen, sulfur or the like, including phosphorus. This invention is intended to cover all the enventualities where a thiol of the type illustrated is reacted with a pyridyl derivative which has an $\alpha,\beta$-unsaturated carbonyl system at the 2-position which can undergo a Michael addition reaction with the thiol.

The $(R)_n$ designation is used here to indicate that one or more groups may be present on either the pyridyl ring or the phenyl ring. This invention also includes the case where each of these R groups is hydrogen. It is expected that any number and combination of substituents may be present on either ring. The only limitation envisioned is that the one of these groups must not interfere with the coupling reaction to a degree as to render the reaction impractical, ie, it does not occur at all, the yield is vanishing small, the wrong product is obtained in an undesirable amount. It should be understood that a given group may be in protected form, for example a carboxylate function may be present in the form of an ester, the acid being regenerated by hydrolytic, catalytic or enzymatic means once the coupling reaction is completed. The invention is that of the use of DBU to affect the coupling of the chloro and the thiol to achieve the thioether and is to be viewed as only so limited.

As for other terms, "aliphatic" is intended to include saturated and unsaturated radicals. This includes normal and branched chains, saturated or mono or poly unsaturated chains where both double and triple bonds may be present in any combination. The phrase "lower alkyl" means an alkyl group of 1 to 6 carbon atoms in any isomeric form, but particularly the normal or linear form. "Lower alkoxy" means the group lower alkyl-O—. "Acyl-lower alkyl" refers to the group (O)C-lower alkyl where the carbonyl carbon is counted as one of the carbons of the 1 to 6 carbons noted under the definition of lower alkyl. "Halo" refers to and means fluoro, chloro, bromo or iodo. The phenyl ring may be substituted with one or more of these radicals. Multiple substituents may be the same or different, such as where there are three chloro groups, or a combination of chloro and alkyl groups and further where this latter combination may have different alkyl radicals in the chloro/alkyl pattern.

Oxides of the pyridyl ring nitrogen may be prepared by means known in the art and as illustrated herein. These are to be considered part of the invention.

If by some combination of substituents, a chiral center is created or another form of an isomeric center is created in a compound of this invention, all forms of such isomer(s) are intended to be covered herein. Compounds with a chiral center may be administered as a racemic mixture or the racemates may be separated and the individual enantiomer used alone.

The compound 1,8-diazabicyclo[5.4.0]undec-7-ene (DBU) is available from Aldrich. To effect the coupling, the thiol or mercaptan is dissolved in a dry polar solvent like acetonitrile to which is added about an equivalent of the chloromethylpyridine adduct to be coupled. Then between 2 to 5 equivalents of DBU as measured against the thiol or mercaptan are added. About 3 equivalents of DBU are preferred. Dry conditions are maintained throughout the course of setting up and running the reaction. An inert atmosphere is used, preferably argon. The reaction is stirred at between about ambient temperature and 100° C. for several hours. The reaction can be made to go in a useful manner by heating the stirred reactants for 2 to 4 hours under an argon gas at a temperature of about 50° C. Thereafter the reaction is cooled and the product, the thioether, is recovered and purified by conventional means.

Preferred products of this reaction are those compounds of formula

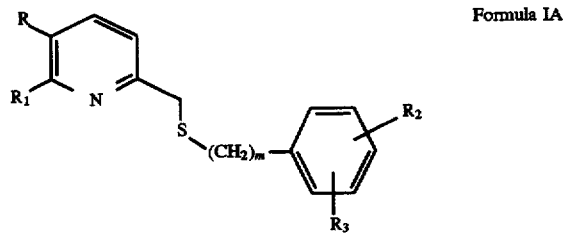

Formula IA or an N-oxide, or a pharmaceutically acceptable salt, where
m is 0–5;
R is $C_1$ to $C_{20}$-aliphatic, unsubstituted or substituted phenyl-$C_1$ to $C_{10}$-aliphatic where substituted phenyl has one or more radicals selected from the group consisting of lower alkoxy, lower alkyl, trihalomethyl, and halo, or R is $C_1$ to $C_{20}$-aliphatic-O—, or R is unsubstituted or substituted phenyl-$C_1$ to $C_{10}$-aliphatic-O— where substituted phenyl has one or more radicals selected from the group consisting of lower alkoxy, lower alkyl, trihalomethyl, and halo;
$R_1$ is —$(CH_2)_xCH=CHCOR_y$, or —$(CH_2)_x$CH=CHCHO, where x is 0–2 and $R_y$ is —OH or an ester thereof or $NH_2$ or a substituted amide derivative thereof;
$R_2$ is H, lower alkoxy, halo, —CN, —$(CH_2)_nR_4$ where n is 0–5, lower alkyl, or $CF_3$;
$R_3$ is H, lower alkoxy, halo, lower alkyl, $CF_3$, —CN, —$(CH_2)_nR_4$ where n is 0–5,
$R_4$ is tetrazol-5-yl or $COR_5$; and
$R_5$ is lower alkoxy, $CH_3(CH_2)_{0-6}CO$ or phenyl$(CH_2)_{0-3}CO$.

The more preferred products are those where R is substituted phenyl-$C_2$ to $C_8$ alkoxy, particularly the unsubstituted-phenyl$(CH_2)_{2-8}$-O— group, or the p-fluoro- or p-methoxyphenyl$(CH_2)_{2-8}$-O— group, or $CH_3(CH_2)_{7-9}$-O—; m is 0–5, most preferably 0, 1, or 2; $R_1$ is $HO_2C$—CH=CH—, or $HO_2C$—$CH_2CH_2$— or a salt, ester or amide derivative thereof. Another sub-group of preferred products are those where $R_2$ and $R_3$ are both hydrogen, both halo, both methyl, or both methoxy. Another preferred set of compounds are those where $R_2$ is $COR_5$ and $R_3$ is hydrogen. The 2,6-dichloro is a preferred product. Specific preferred products are:

(E)-methyl 3-[3-[4-(4-methoxyphenyl)butyloxy]-6-[(2,6-dichlorophenylthio)methyl]-2-pyridinyl]-2-propenoate, (E)-methyl 3-[3-[4-(4-methoxyphenyl)butyloxy]-6-[phenylthiomethyl]-2-pyridinyl]-2-propenoate.

(E)-methyl 3-[3-[2-(4-methoxyphenyl)ethyloxy]-6-[(2,6-dichlorophenylthio)-methyl]-2-pyridinyl]-2-propenoate, (E)-methyl 3-[3-[2-(4-fluorophenyl)ethyloxy]-6-[(2,6-dichlorophenylthio)methyl]-2-pyridinyl]-2-propenoate, or (E)-methyl 3-[3-[8-(4-methoxyphenyl)octyloxy]-6-[(3-carbomethoxy-benzylthio)methyl]-2-pyridinyl]-2-propenoate.

SYNTHESIS

Several methods, variations on the same process, have been used for preparing these compounds. In general, the approach taken was to first make the intermediates needed to make the R group, then to prepare the phenyl intermediate needed for forming the core structure of formula I; the pyridyl intermediate was then prepared and reacted with the phenyl intermediate to form the core structure. Salts, free acids, amides, alternative esters and the like were then prepared.

As noted, the first step was to make the intermediates needed for forming those R groups where the intermediates were not available commercially. This chemistry is illustrated for the case of the substituted phenyl-$C_1$ to $C_{10}$-aliphatic-O— groups. The same or similar chemistry has been disclosed in published patent applications, for example PCT international application numbers PCT/US91/03772, PCT/US91/03940, and PCT/US91/03399. The chemistries set out in those documents can be used in place of or in conjunction with those given here to prepare the R groups of formula I.

Usually the substituted chloromethylpyridine is prepared next, as opposed to the thiol intermediate, but this is not critical to the practice of the invention. Making the substituted 6-chloromethylpyridyl intermediate can begin with the starting compound and the chemistry disclosed in the PCT application PCT/US91/03772 and the other PCT cases cited above. The chemistry set out in the '03772 case can be used to convert the starting material, 2,6-lutidine-$\alpha^2$,3-diol, to, for example, the 2-(E-2-carboxymethylethenyl)-3-[4-(4-methoxyphenyl)butyloxy]-6-chloromethylpyridine. This is illustrated in Scheme I given below. Novel chemistry, both conditions and the reagent DBU, are then used to couple the thiophenol with the chloromethyl substituted pyridine in order to make the basic structure of formula I. Base, or acid, can then be used to hydrolyze any ester group, if so desired. A free acid can be obtained from the salt by acidifying a solution of the salt. Esters and amides can be prepared using standard reaction conditions and reagents. Tetrazoles are prepared from the corresponding acid halide, e.g., the acid chloride, by literature methods.

Using the precursors prepared as per the noted PCT applications or which have been purchased from a commercial source, and the steps outlined in Scheme I, can be used to prepare compounds of formula I.

Scheme I

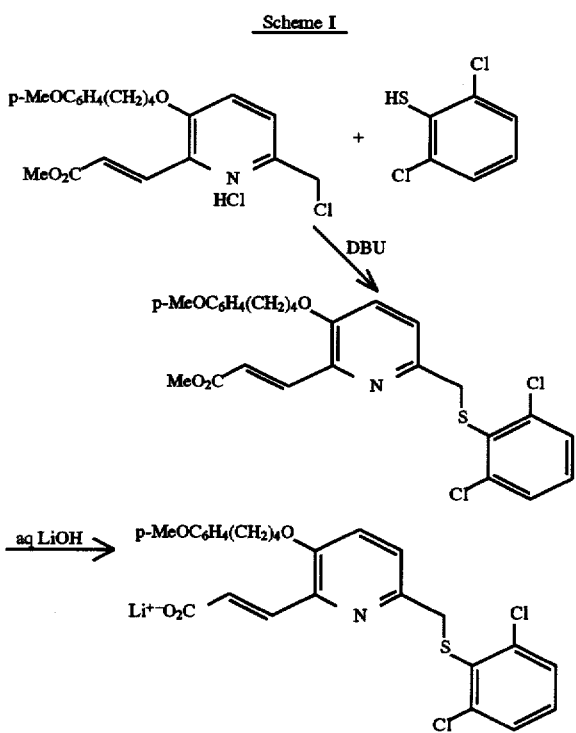

A general description of the conditions and reagents which can be used for converting the diol to the 6-(chloromethyl)pyridine compound can be found in PCT application number PCT/US91/03772. That description of the generalized case for each step is incorporated herein by reference along with the specific chemistry set out in the Examples of that application.

A number of thiophenols and thioalkylphenyl compounds useful for making the right hand portion of formula I can be purchased from commercial sources. A list, not intended to be exhaustive, is as follows: 2,5-dichlorothiophenol, 2,6-dimethylthiophenol,2-chloro-6-fluorobenzyl mercaptan, and 2,4-difluorobenzyl thiol. Other thiols can be made by published chemistry; that chemistry involves converting a haloalkylphenyl (the bromo form is preferred) compound to the corresponding mercaptan by treating the bromo compound with thiourea followed by base hydrolysis. Alternatively the thiophenols can be prepared by thermal rearrangement of the corresponding thiocarbamate followed by hydrolysis.

Coupling the thiol with the chloromethylpyridyl compound using a novel method which employs 1,8-diazabicyclo[5.4.0]undec-7-ene (DBU) and an appropriate solvent, for example $CH_3CN$. Moisture is excluded from the system and an inert gas is used, for example argon. A slightly elevated temperature is preferred, one that is about 50° C. or so; the coupling reaction is complete in about 3 hours.

Once the core structure is prepared any ester can be hydrolyzed with acid or base, base is preferred, or that acid can be converted to another ester, an amide or another salt.

SPECIFIC EMBODIMENTS

The following examples are given to illustrate how to make and use the compounds of this invention. These Examples are just that, examples, and are not intended to circumscribe or otherwise limit the scope of this invention. Reference is made to the claims for defining what is reserved to the inventors.

EXAMPLE 1

(E)-Lithium 3-[3-[4-(4-methoxyphenyl)butyloxy]-6-[(2,6-dichlorophenylthio)methyl]-2-pyridinyl]-2-propenoate 2A (E)-Methyl 3-[3-[4-(4-methoxyphenyl)butyloxy]-6-[(2,6-dichlorophenylthio)methyl]-2-pyridinyl]-2-propenoate. 2,6-Dichlorothiophenol (53 mg, 0.297 mmol, Aldrich) was dissolved in dry MeCN (0.60 mL) and treated with 2-(E-2-carboxymethylethenyl)-3-[4-(4-methoxyphenyl)butyloxy]-6-chloromethylpyridine hydrochloride (115 mg, 0.270 mmol) and 1,8-diazabicyclo[5.4.0]undec-7-ene (DBU, 0.142 mL, 0.949 mmol). The reaction was stirred under an atmosphere of argon at 50° C. for 3 h. The reaction solution was diluted with EtOAc and washed with $H_2O$ and brine and dried ($MgSO_4$). Purification by flash column chromatography (silica, EtOAc: $CH_2Cl_2$: hexane, 10: 15: 75) gave a colorless waxy solid: $^1H$ NMR (250 MHz, $CDCl_3$) δ7.94 (d, J=15.7 Hz, 1H, vinyl), 7.31 (d, J=7.6 Hz, 2H, aryl), 7.13 (m,4H, aryl, pyridyl), 7.11 (α, J=8.4 Hz, 1H, pyridyl), 6.86 (d, J=8.7 Hz, 2H, phenyl), 6.69 (d, J=15.7 Hz, 1H, vinyl), 4.14 (s, 2H, $CH_2$—S), 3.97 (t, J=6.1 Hz, 2H, $CH_2$—O), 3.80 (s, 3H, OMe), 3.78 (s, 3H, methyl ester), 2.63 (t, J=7.2 Hz, 2H, benzylic), 1.81 (m, 4H, $CH_2CH_2$); analysis calcd. for $C_{27}H_{27}Cl_2NO_4S$: C, 60.90; H, 5.11; N, 2.63; found: C, 60.61; H, 5.01; N, 2.57; MS (ES+): 532.0 (M+H).

Proceeding in a similar manner, but substituting for the intermediates listed in 1A and 1B the appropriate chloromethylpyridine and thiophenol or mercaptoalkylphenyl adducts, the following compounds can be prepared:

(E)-methyl 3-[3-[8-(4-methoxyphenyl)octyloxy]-6-[(3-carbomethoxybenzylthio)-methyl]-2-pyridinyl]-2-propenoate, (E)-methyl 3-[3-[4-(4-methoxyphenyl)butyloxy]-6-[phenylthiomethyl]-2-pyridinyl]-2-propenoate, and (E)-methyl 3-[3-[4-(4-methoxyphenyl)butyloxy]-6-[(2,6-dichlorophenylthio)methyl]-2-pyridinyl]-2-propenoate.

2B (E)-Lithium 3-[3-[4-(4-methoxyphenyl)butyloxy]-6-[(2,6-dichlorophenylthio)methyl]-2-pyridinyl]-2-propenoate. (E)-Methyl 3-[3-[4-(4-methoxyphenyl)butyloxy]-6-[(2,6-dichlorophenylthio)methyl]-2-pyridinyl]-2-propenoate (65 mg, 0.122 mmol) was dissolved in THF (1.0 mL) and MeOH (0.50 mL) and treated with 1.0M LiOH (0.25 mL, 0.25 mmol). The reaction was stirred under an argon atmosphere for 20 h. The solvent was evaporated and the product purified by Reversed Phased MPLC (RP-18 silica, $H_2O$-MeOH gradient). Lyopphilization yielded a colorless amorphous solid: $^1H$ NMR (250 MHz, $d^4$-MeOH) δ7.68 (d, J=15.7 Hz, 1H, vinyl), 7.37 (d, J=7.6 Hz, 2H, aryl), 7.13 (m, 4H, aryl, pyridyl), 7.02 (d, J=8.4 Hz, 1H, pyridyl), 6.82 (d, J=15.7 Hz, 1H, vinyl), 6.81 (d, J=8.7 Hz, 2H, phenyl), 4.13 (s, 2H, $CH_2$—S), 4.00 (t, J=6.1 Hz, 2H, $CH_2$—O), 3.75 (s, 3H, OMe), 2.62 (t, J=7.2 Hz, 2H, benzylic), 1.80 (m, 4H, $CH_2CH_2$); analysis calcd. for $C_{26}H_{24}Cl_2NO_4SLi.15/8\ H_2O$: C, 55.95; H, 5.01; N, 2.51; found: C, 55.75; H, 4.58; N, 2.36; MS (ES+): 518.0 (M+H, free acid).

What is claimed is:

1. A process for making a compound of formula I

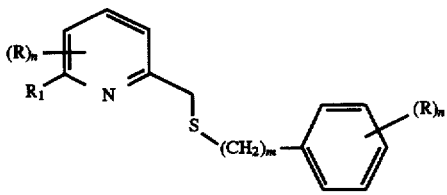

where the $R_1$ is —$(CH_2)_xCH$=$CHCOR_y$, or —$(CH_2)_x$CH=CHCHO, where x is 0–2 and $R_y$ is —OH or an ester thereof or $NH_2$ or a substituted amide derivative thereof; and the designation $(R)_n$ is hydrogen or one or more non-hydrogen radicals covalently bonded to the pyridyl and phenyl rings and n is 1–2 when $(R)_n$ is not hydrogen, and m is 0–5; which process comprises coupling a chloromethylpyridine of formula II with a thiol of formula III in the presence of 2 to 5 equivalents of 1,8-diazabicyclo[5.4.0]undec-7-ene (DBU) under an inert gas at a temperature between about ambient and 100° C. for a period sufficient to effect the coupling;

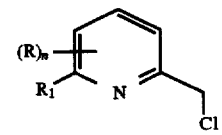

Formula II

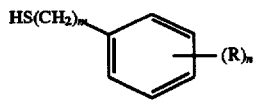

Formula III where $R_1$ is defined above, m is 0–5 and $(R)_n$ is hydrogen or one or more radicals which can be substituted on either the pyridyl or phenyl ring and which does not have a functional group which interferes with the coupling reaction.

2. The process of claim 1 where about 3 equivalents of DBU is used and the reaction is carried out in acetonitrile under argon at a temperature of about 50° C. for 2 to 4 hours.

3. A process for making a compound of formula IA

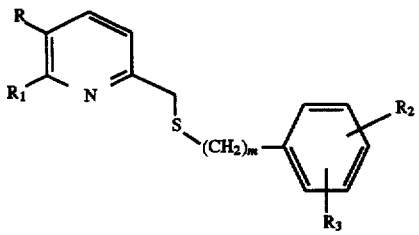

IA or an N-oxide, or a pharmaceutically acceptable salt, where R is $C_1$ to $C_{20}$-alkyl, unsubstituted or substituted phenyl-$C_1$ to $C_{10}$-alkyl where substituted phenyl has one or more radicals selected from the group consisting of lower alkoxy, lower alkyl, trihalomethyl, and halo, or R is $C_1$ to $C_{20}$-alkyl-O—, or R is unsubstituted or substituted phenyl-$C_1$ to $C_{10}$-alykl-O— where substituted phenyl has one or more radicals selected from the group consisting of lower alkoxy, lower alkyl, trihalomethyl, and halo;

$R_1$ is —$(CH_2)_xCH$=$CHCOR_y$, or —$(CH_2)_x$CH=CHCHO, where x is 0–2 and $R_y$ is —OH or an ester thereof or $NH_2$ or a substituted amide derivative thereof;

$R_2$ is H, lower alkoxy, halo, —CN, —$(CH_2)_nR_4$ where n is 0–5, lower alkyl, or $CF_3$;

$R_3$ is H, lower alkoxy, halo, lower alkyl, CF3, —CN, —$(CH_2)_nR_4$ where n is 0–5, $R_4$ is tetrazol-5-yl or $COR_5$; and $R_5$ is lower alkoxy, $CH_3(CH_2)_{0-6}CO$ or phenyl $(CH_2)_{0-3}CO$;

which process comprises coupling a chloromethylpyridine of formula IIA with a thiol of formula IIIA in the presence of 2 to 5 equivalents of 1,8-diazabicyclo [5.4.0]undec-7-ene (DBU) under an inert gas at a temperature between about ambient and 100° C. for a period sufficient to effect the coupling;

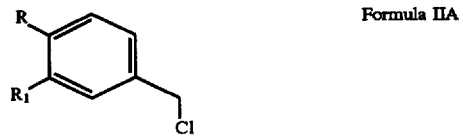

Formula IIA

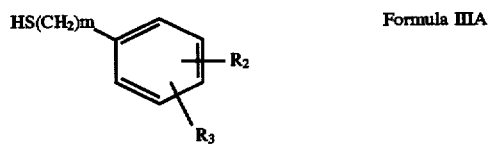

Formula IIIA wherein R, $R_1$, $R_2$, $R_3$ and m are the same as defined above.

4. The process of claim 3 wherein R is substituted phenyl-$C_2$ to $C_8$ alkoxy, particularly the unsubstituted-phenyl$(CH_2)_{2-8}$—O— group, or the p-fluoro- or p-methoxyphenyl$(CH_2)_{2-8}$—O— group, or $CH_3(CH_2)_{7-9}$—O—; m is 0, 1 or 2; $R_1$ is $HO_2C$—CH=CH—, or $HO_2C$—$CH_2CH_2$— or a salt, ester or amide derivative thereof, and $R_2$ and $R_3$ are both hydrogen, halo, methyl, or methoxy.

5. The process of claim 3 where $R_2$ is $COR_5$ and $R_3$ is hydrogen.

6. The process of claim 3 where $R_2$ and $R_3$ are both chloro.

7. The process of claim 3 wherein the compound is (E)-methyl 3-[3-[4-(4-methoxyphenyl)butyloxy]-6-[(2,6-dichlorophenylthio)methyl]-2-pyridinyl]-2-propenoate, (E)-methyl 3-[3-[4-(4-methoxyphenyl)butyloxy]-6-[phenylthiomethyl]-2-pyridinyl]-2-propenoate. (E)-methyl 3-[3-[2-(4-methoxyphenyl)ethyloxy]-6-[(2,6-dichlorophenylthio)-methyl]-2-pyridinyl]-2-propenoate, (E)-methyl 3-[3-[2-(4-fluorophenyl)ethyloxy]-6-[(2,6-dichlorophenylthio)methyl]-2-pyridinyl]-2-propenoate, or (E)-methyl 3-[3-[8-(4-methoxyphenyl)octyloxy]-6-[(3-carbomethoxy-benzylthio)methyl]-2-pyridinyl]-2-propenoate.

* * * * *